US010088387B2

(12) United States Patent
Jin et al.

(10) Patent No.: US 10,088,387 B2
(45) Date of Patent: Oct. 2, 2018

(54) BRAKE BEAM FATIGUE TEST STAND (71) Applicant: CRRC QINGDAO SIFANG ROLLING STOCK RESEARCH INSTITUTE CO., LTD., Qingdao (CN)

(72) Inventors: Xing Jin, Qingdao (CN); Yunkang Luo, Qingdao (CN)

(73) Assignee: CRRC QINGDAO SIFANG ROLLING STOCK RESEARCH INSTITUTE CO., LTD., Shandong (CN)

( * ) Notice: Subject to any disclaimer, the term of this patent is extended or adjusted under 35 U.S.C. 154(b) by 0 days.

(21) Appl. No.: 15/546,274

(22) PCT Filed: Oct. 14, 2016

(86) PCT No.: PCT/CN2016/102117
§ 371 (c)(1),
(2) Date: Jul. 25, 2017

(87) PCT Pub. No.: WO2017/088602
PCT Pub. Date: Jun. 1, 2017

(65) Prior Publication Data
US 2018/0017465 A1    Jan. 18, 2018

(30) Foreign Application Priority Data

May 18, 2016 (CN) .......................... 2016 1 0330514
May 18, 2016 (CN) .......................... 2016 1 0330961

(51) Int. Cl.
*G01N 3/12* (2006.01)
*G01M 13/02* (2006.01)
(Continued)

(52) U.S. Cl.
CPC ......... *G01M 13/027* (2013.01); *G01L 27/005* (2013.01); *G01M 13/00* (2013.01);
(Continued)

(58) Field of Classification Search
CPC ..... G01M 13/027; G01L 27/005; G01N 3/12; G01N 2203/0005; G01N 2203/0073
(Continued)

(56) References Cited

U.S. PATENT DOCUMENTS 4,800,748 A    1/1989  Fischer et al. ............... 73/865.9
5,197,333 A *  3/1993  Garcia-Gardea ....... G01M 7/00
                                                    73/666

FOREIGN PATENT DOCUMENTS

CN       2635480 Y      8/2004
CN     201138293 Y     10/2008
(Continued)

OTHER PUBLICATIONS

International Search Report of corresponding International PCT Application No. PCT/CN2016/102117, dated Jan. 26, 2017.
(Continued)

*Primary Examiner* — Jonathan Dunlap
(74) *Attorney, Agent, or Firm* — J.C. Patents (57) ABSTRACT The present invention discloses a brake beam fatigue test stand, for simultaneously testing a fatigue strength of two brake beams, comprise: a base, and four upright columns vertical to the base and arranged on the base at intervals; a first tangential load actuator is mounted vertically between the first upright column and the second upright column, with simulated wheels being mounted on a front side and a rear side of a bottom of the actuator; a pressure load actuator is mounted vertically between the second upright column and the third upright column; a second tangential load actuator is mounted vertically between the third upright column and
(Continued)

the fourth upright column, with simulated wheels being mounted on a front side and a rear side of a bottom of the actuator; the stiffness of the test stand in vertical and transverse directions is enhanced.

20 Claims, 9 Drawing Sheets

(51) Int. Cl.
    *G01M 13/00* (2006.01)
    *G01M 17/007* (2006.01)
    *G01L 27/00* (2006.01)
(52) U.S. Cl.
    CPC ............ *G01M 17/007* (2013.01); *G01N 3/12* (2013.01); *G01N 2203/0005* (2013.01); *G01N 2203/0073* (2013.01)
(58) Field of Classification Search
    USPC .......... 73/115.07, 117.03, 862.381, 862.451, 73/862.637; 188/219.1–233.7
    See application file for complete search history.

(56) References Cited

FOREIGN PATENT DOCUMENTS

| | | |
|---|---|---|
| CN | 201673096 U | 12/2010 |
| CN | 102262004 A | 11/2011 |
| CN | 104297046 A | 1/2015 |
| CN | 104990713 A | 10/2015 |
| CN | 204740133 U | 11/2015 |
| CN | 105784391 A | 7/2016 |
| JP | 2001-153774 A | 6/2001 |
| JP | 2016-020880 A | 2/2016 |
| RU | 97 196 U1 | 8/2010 |

OTHER PUBLICATIONS

China National Standards No. TB/T 1978-2007, "Assembled brake beam for railway freight car" Published by the Ministry of Railway of the People's Republic of China; Aug. 13, 2007, p. 11-15.
The extended European Search Report of corresponding European patent application No. 16867828.2-1557, dated Nov. 2, 2017.

* cited by examiner

BRAKE BEAM FATIGUE TEST STAND

CROSS-REFERENCE TO RELATED APPLICATION

This application is a national phase application of international application No. PCT/CN2016/102117 filed on Oct. 14, 2016, which in turn claims the priority benefits of Chinese application No. 201610330514.2, filed on May 18, 2016 and application No. 201610330961.8, filed on May 18, 2016. The contents of these prior applications are hereby incorporated by reference in their entirety.

TECHNICAL FIELD

The present invention belongs to the technical field of rail transit, and in particular to a fatigue test stand for rail wagon brake beams.

BACKGROUND OF THE PRESENT INVENTION

Figure 1:
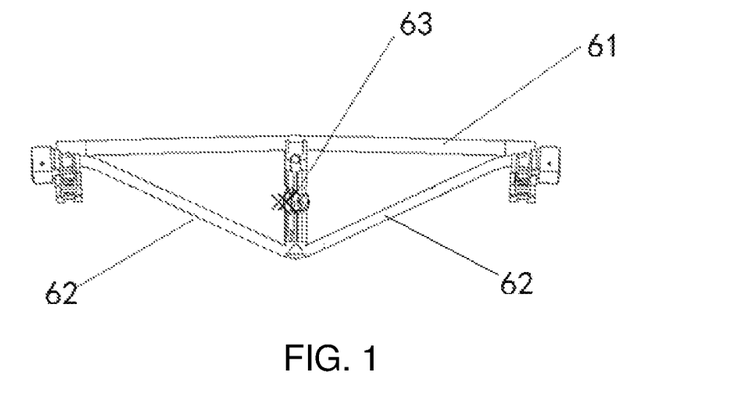
FIG. 1 is a structural schematic diagram of a brake beam.

Rail wagon brake beam is the most important part in a basic brake device for rail wagons. When a vehicle brakes, the brake beam can transfer the brake force generated by a brake cylinder to brake shoes, so as to achieve braking of the vehicle. FIG. 1 is a schematic structure diagram of a brake beam. The brake beam 6 is a triangle-like beam, including a cross rod 61 in the horizontal direction and diagonal rods 62 provided at two end portions of the cross rod 61; the diagonal rods 62 are inclined downward to be intersected at one point; a beam strut 63 is uprightly provided between the point and the cross rod 61; and when in normal use, the brake beam 6 is horizontally arranged.

To ensure the application reliability of the brake beam, a fatigue test is to be performed on the brake beam. When a fatigue test is performed on the brake beam, two ends of the cross rod 61 of the brake beam respectively pass through two mounting holes in the middle of two brake shoe holders and are respectively mounted on the brake shoe holders. A simulated brake shoe is mounted on a simulated wheel pair by a brake shoe holder, and the coordination between the simulated brake shoe and a simulated wheel tread should be in accordance with the actual conditions. The mounting between the simulated brake shoe and the brake shoe holder and the mounting between the simulated brake shoe and the simulated wheels are firm, so as to ensure that there is no sliding during the loading process. The simulated wheel should have a degree of freedom for rotating around the axis thereof and a degree of linear displacement freedom for restricting an end of the brake beam moving along the tangential direction of the wheel treading surface. After the brake beam is properly mounted, a pressure load and a tangential load are simultaneously applied to the brake beam, wherein the pressure load acts on a beam strut pin hole, varying from 0 kN to 104.5 kN; and the tangential load produces between the simulated wheel tread and the two simulated brake shoes, varying from −43.7 kN to 43.7 kN.

At present, there are three types of brake beam fatigue test stands. The first type is characterized by mounting brake beams in the transverse direction. With regard to this type, although the direction in which the brake beam is placed on the test stand is consistent with that during the practical application, the fatigue test can be performed on only one brake beam each time, thus having a low test efficiency. The second type is characterized by placing the brake beam in the transverse direction. With regard to the second type, two brake beams can be simultaneously tested, and a pressure load is applied by a transverse actuator and a tangential load is applied by a vertical actuator. However, a test stand of this type occupies a large space, and a load is to be applied respectively in transverse and vertical directions. In this way, the test stand has a complicated structure, and since it is unable to replace simulated wheels of different wheel diameters, the test stand cannot be adapted to brake beams of different types. The third type is a gantry-type test stand. With regard to the third type, brake beams are placed in a vertical direction, and two brake beams can be simultaneously tested; and both the pressure load and the tangential load are applied by a vertical actuator. The whole structure of a test stand of this type has a relatively low stiffness, and a relatively high deformation will thus occur during the loading process in the fatigue test, and consequently, the improvement to the test loading frequency and test efficiency is influenced. At present, the maximum test loading frequency is 2.3 HZ. The gantry of the test stand has a low strength, and fatigue cracks are likely to occur on the gantry structure body. There are too many gaps in the connection portion between the test stand and the brake beam to be tested, and it is difficult to adjust those gaps.

SUMMARY OF THE PRESENT INVENTION

The present application provides a brake beam fatigue test stand which is of a gantry structure having diagonal braces, by which the stiffness of the test stand in vertical and transverse directions can be enhanced; only a slight deformation occurs during the test, the test loading frequency of the test stand is further enhanced, and the test efficiency is thus improved.

To achieve the above mentioned purposes, the present application employs the following technical solutions.

A brake beam fatigue test stand, for simultaneously testing the fatigue strength of two brake beams, comprises: a base, and four upright columns vertical to the base and arranged on the base at intervals; from a left side to a right side of the base successively, there are a first upright column, a second upright column, a third upright column and a fourth upright column, wherein a first tangential load actuator capable of applying a tangential load is mounted vertically between the first upright column and the second upright column, with simulated wheels being mounted on a front side and a rear side of a bottom of the first tangential load actuator; a pressure load actuator capable of applying a pressure load is mounted vertically between the second upright column and the third upright column; a second tangential load actuator capable of applying a tangential load is mounted vertically between the third upright column and the fourth upright column, with simulated wheels being mounted on a front side and a rear side of a bottom of the second tangential load actuator; the second tangential load actuator and the first tangential load actuator are symmetrically arranged by taking the pressure load actuator as a center; and the two brake beams are uprightly mounted on a front side and a rear side of the upright columns, with two ends of the brake beam being supported on treads of the simulated wheels.

Preferably, a tangential load distribution beam capable of receiving a tangential load is provided on each bottom of the first tangential load actuator and the second tangential load actuator, and each of the tangential load distribution beam is horizontally arranged in front and rear direction and is vertical to the upright columns; two ends of the tangential load distribution beam are respectively connected to the simulated wheels arranged on the front side and the rear side of the upright columns, to distribute a tangential load to the simulated wheels arranged on the two sides of the tangential load actuators.

Preferably, the simulated wheel is drum-shaped, and an upper arc surface and a lower arc surface of the drum-shaped simulated wheel are arc treads with different diameters, so as to simulate wheels of two different diameters on a same simulated wheel.

Preferably, baffles are provided in a front wheel and a rear wheel of the simulated wheels; and connection beams mountable with the tangential load distribution beam are mounted in the baffles and fixed by wedges.

Preferably, a simulated brake shoe matched with the radian of the tread is provided on the tread of the simulated wheel, a brake shoe holder is provided on the simulated brake shoe, and a gap elimination device is provided between the simulated wheel and the brake shoe holder so as to eliminate the gap between the brake shoe holder and the simulated wheel.

Preferably, a pressure load distribution beam capable of distributing a pressure load is provided on the bottom of the pressure load actuator; the pressure load distribution beams is horizontally arranged in front and rear direction and is vertical to the upright columns, wherein round strut pins capable of having brake beam struts mounted thereon are mounted at two ends of the pressure load distribution beam; and the beam struts of the brake beam are mounted on the round strut pins to receive the pressure load distributed by the pressure load actuator.

Preferably, U-shaped connection blocks are provided at both ends of the pressure load distribution beam, and an inverted V-shaped strut connection block is provided above each U-shaped connection block; two ends of one U-shaped connection block are connected to two ends of one strut connection blocks; a round strut pin is provided on the strut connection block; the round strut pin is configured to maintain the beam strut of the brake beam vertical and transfers the pressure load to the brake beam.

Preferably, a feedback device capable of performing feedback tests on the tangential load is provided on the bottom of the first tangential load actuator, and the feedback device comprises a sensor capable of sensing the intensity of a tangential load feedback force.

Preferably, diagonal braces are provided on the front side and the rear side of the upright column.

Preferably, simulated chutes are provided on the brake beam fatigue test stand, and the two ends of the brake beam pass through the brake shoe holder to be located in the simulated chutes. Specifically, guide bushings at the two ends of the brake beam are located in the simulated chutes. In actual tests and in order to better secure a brake beam on the test stand, both the simulated chutes and the guide bushings at two ends of the brake beam are used, as they belong to the prior art, they will not be repeated here.

Preferably, the diagonal braces include a first group of diagonal braces located in front of and behind the first upright column and a second group of diagonal braces located in front of and behind the fourth upright column; and the simulated chute is located on a bracket between the first upright column and the first group of diagonal braces or on a bracket between the fourth upright column and the second group of diagonal braces.

Preferably, ladders are provided at a left side of the first upright column and a right side of the fourth upright column.

Preferably, a platform is horizontally provided on the top of the upright columns A gap elimination device is provided, which can be configured to eliminate a gap between the simulated wheel and the brake shoe holder during a brake beam fatigue stand test, comprises a connection block capable of connecting the simulated wheel and the brake shoe holder; a top part of the connection block is a trapezoidal end matched with a trapezoidal groove on the brake shoe holder, and two sides of the trapezoidal end are slope surfaces; an open groove is formed on the slope surface; and an adjustment block which is movable in the open groove is provided in the open groove, and a gap between a side of the top part of the connection block and the brake shoe holder is eliminated by moving the position of the adjustment block inside the open groove.

Preferably, a protrusion is provided on an inner surface of the adjustment block, and the slope surface has a slope direction opposite to a slope direction of the inner surface of the adjustment block. More preferably, the open groove has a slope direction opposite to a slope direction of the protrusion, and they work together to eliminate the gap.

Preferably, the open groove is arranged along the slope direction of the slope surface, the open groove is a semi-arc groove, and a semi-cylindrical protrusion matched with the open groove is provided on the adjustment block.

Preferably, an adjustment plate capable of preventing the adjustment block from loosening is mounted on a side of the trapezoidal end of the connection block, and the connection block and the adjustment plate are connected by bolts.

Preferably, there are two open grooves formed on the slope surface at each side of the connection block, so as to increase the contact area between the gap elimination device and the brake shoe holder.

Preferably, a top surface of the connection block is an inclined surface consistent with a mounting surface of the brake shoe holder.

Compared with the prior art, the present application has the following advantages and beneficial effects.

First, for the brake beam fatigue test stand of the present application, a gantry layout with diagonal braces is used, so that the stiffness of the test stand in vertical and transverse directions can be enhanced, only a slight deformation occurs during the test, the test loading frequency of the test stand is further enhanced, and the test efficiency is thus improved. Meanwhile, the brake beam fatigue test stand has a relatively high strength and a low stress during the test. In this way, the fatigue life of the test stand structure itself can be greatly enhanced and the service life of the test stand can be prolonged.

Second, for the brake beam fatigue test stand of the present application, by providing wheels with different diameters on two side surfaces of the simulated wheels, wheels with two different diameters can be simultaneously simulated. When test pieces of different types are to be replaced, it is not necessary to remove and then assemble simulated wheels with different diameters. Simulated wheels of different diameters can be replaced simply and conveniently just by rotating the simulated wheels.

Third, the brake beam fatigue test stand of the present application has definite routes for transferring the pressure load and tangential load; with the use of the tangential load feedback device and after the transferred tangential load is applied to the brake beam, the value thereof can be verified. The testing personnel can apply a load to the actuator or adjust the structure of the test stand in time, so as to ensure the accuracy of test results.

Fourth, for the brake beam fatigue test stand of the present application, the arrangement of the gap elimination device between the brake shoe holder and the simulated wheel increases the test loading frequency and improves the reliability of test results.

Fifth, the gap elimination device in the brake beam fatigue test stand eliminates the gap by the coordination of the connection block of the open groove having a slope and the adjustment block having an opposite slope. In this way, the stepless adjustment to the position of the adjustment block and the transfer of loads are both realized.

Sixth, for the gap elimination device in the brake beam fatigue test stand, an upper adjustment block and a lower adjustment block are provided on each side surface of the connection block to increase the contact area between the plane portion on the back of the adjustment block and the trapezoidal groove of the brake shoe holder. In this way, better restriction is provided and the transfer of loads is realized.

Seventh, for the gap elimination device in the brake beam fatigue test stand, the connection block and the adjustment block come into cylindrical coordination, so that the cylindrical adjustment block has a certain rotational degree of freedom and is thus adapted to the irregularity of the trapezoidal groove of the brake shoe holder due to a manufacturing tolerance and fitted with the trapezoidal groove of the brake shoe holder.

Eighth, for the gap elimination device in the brake beam fatigue test stand, an adjustment plate is mounted at an end portion of the connection block, so that the adjustment block after the gap adjustment can be fixed, and the unexpected sliding of the adjustment block due to vibration is thus avoided.

BRIEF DESCRIPTION OF THE DRAWINGS

FIG. 11 is a front view of a connection block.
in which:
1 base; 2 simulated wheel; 21 simulated brake shoe; 22 gap elimination device; 221 adjustment plate; 222 connection block; 2221 open groove; 2222 mounting hole; 2223 trapezoidal end; 2224 slope surface; 223 adjustment block; 2231 protrusion; 224 adjustment bolt; 225 bolt; 23 connection beam; 231 wedge; 24 tangential load distribution beam; 25 U-shaped groove; 3 first tangential load actuator; 4 second tangential load actuator; 5 pressure load actuator; 51 pressure load distribution beam; 52 round strut pin; 53 U-shaped connection block; 54 strut connection block; 6 brake beam; 61 cross rod; 62 diagonal rod; 63 beam strut; 7 feedback device; 81 first upright column; 82 second upright column; 83 third upright column; 84 fourth upright column; 9 diagonal brace; 10 brake shoe holder; and 101 trapezoidal groove.

DETAILED DESCRIPTION OF THE PRESENT INVENTION

The present application will be described in detail below by exemplary embodiments. However, it should be understood that, unless otherwise stated, elements, structures and features in one embodiment can be beneficially combined into other embodiments. Meanwhile, in the description of the present application, it should be noted that orientations or positional relationships indicated in the brake beam fatigue test stand by terms such as "upper", "lower", "front", "rear", "top", "bottom" are the positional relationships illustrated on the basis of FIG. 2. Those terms are used merely for ease of describing the present application and simplifying the description, not for indicating or implying that the involved device or element must have a specific orientation or be constructed and operated in the specific orientation. Therefore, they shall not be considered as limitations to the present application. In the drawings provided by the present application, view directions of FIGS. 3 to 7, FIG. 9 and FIG. 10 can be considered to be consistent with each other. In addition, terms such as "first", "second" and "third" and so on are merely used for description and cannot be understood as indicating or implying the relative importance.

Figure 2:
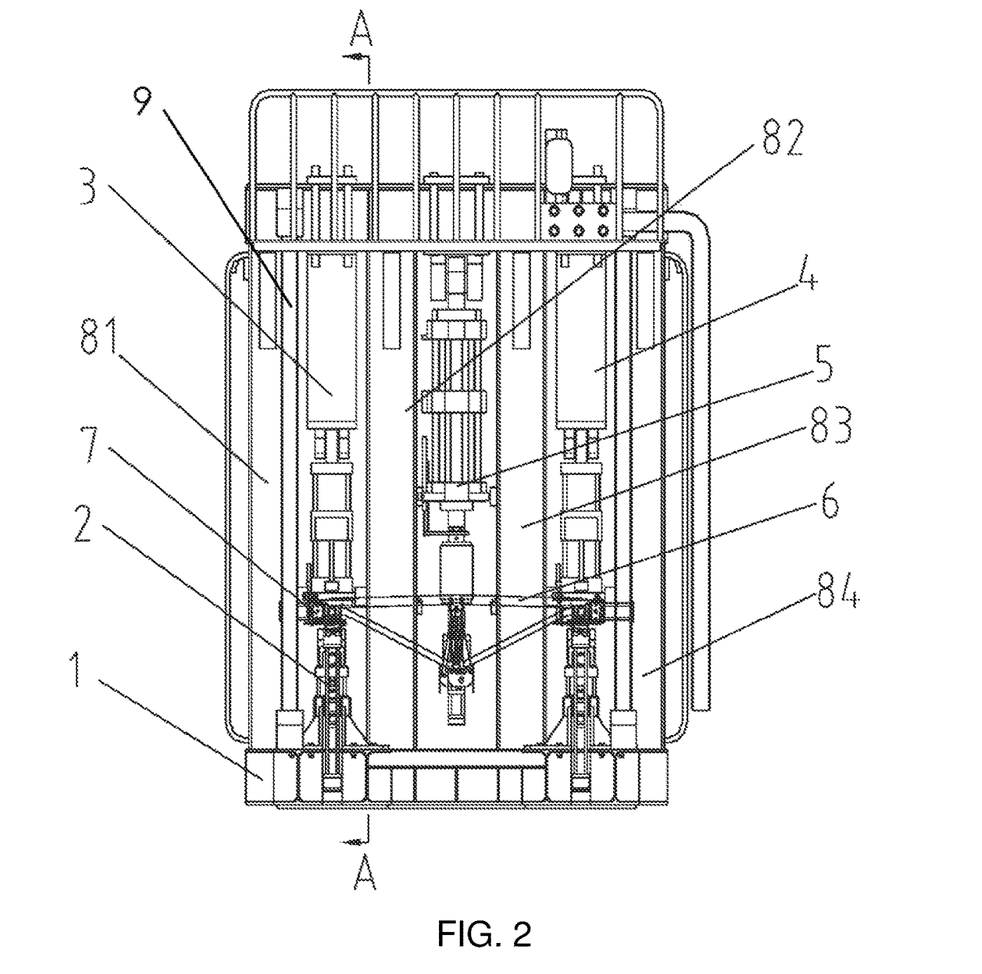
FIG. 2 is a front view of a brake beam fatigue test stand.

FIG. 2 is a front view of a brake beam fatigue test stand in the present application. A brake beam fatigue test stand, for simultaneously testing the fatigue strength of two brake beams, comprises: a base 1, and four upright columns vertical to the base 1 and arranged on the base 1 at intervals; from the left to the right of the base 1 successively, there are a first upright column 81, a second upright column 82, a third upright column 83 and a fourth upright column 84, with three intervals being formed among the four upright columns which are interval arranged, wherein a first tangential load actuator 3 capable of applying a tangential load is mounted vertically between the first upright column 81 and the second upright column 82, with simulated wheels 2 being symmetrically mounted on a front side and a rear side of a bottom of the first tangential load actuator 3; a pressure load actuator 5 capable of applying a pressure load is mounted vertically between the second upright column 82 and the third upright column 83; a second tangential load actuator 4 capable of applying a tangential load is mounted vertically between the third upright column 83 and the fourth upright column 84, with simulated wheels 2 being symmetrically mounted on a front side and a rear side of a bottom of the second tangential load actuator 4; the second tangential load actuator 4 and the first tangential load actuator 3 are symmetrically arranged by taking the pressure load actuator 5 as a center; and the two brake beams 6 are uprightly mounted on a front side and a rear side of the upright columns. In FIG. 2, only the brake beam 6 located on the front side is visible, and two ends of the brake beam 6 are supported on treads of the two simulated wheels 2. As one embodiment, a simulated brake shoe 21 is mounted on the simulated wheel 2, and a brake shoe holder 10 is provided on the simulated brake shoe 21; and the brake beam 6 is arranged on the simulated brake shoes 21 by the brake shoe holders 10.

In the arrangement as mentioned above, "arranged vertically" means "arranged to be vertical to the ground"; the stiffness of the brake beam fatigue test stand in the vertical direction is higher than that of a structure having two upright columns in the vertical direction in the prior art, and this helps to improve the loading frequency.

Figure 3:
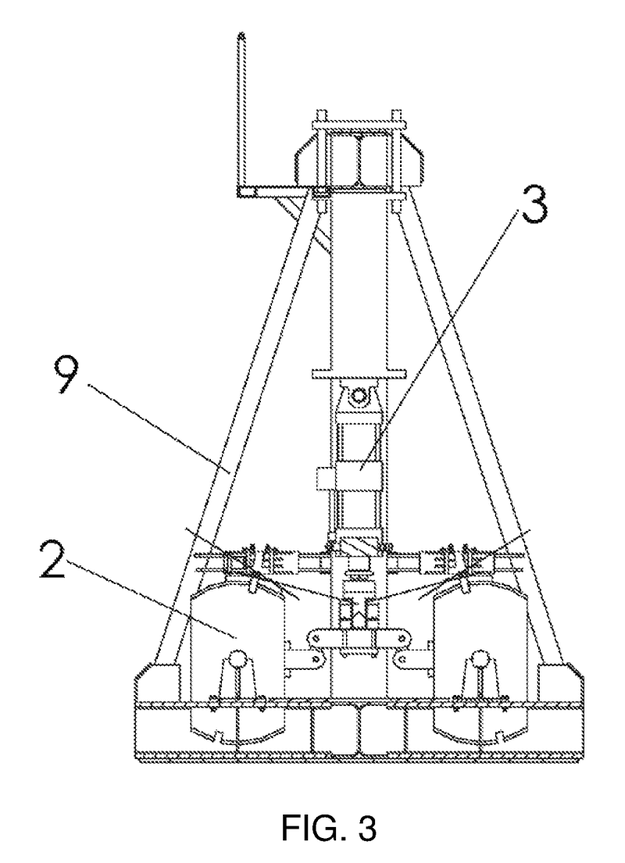
FIG. 3 is a sectional view in a direction A-A of FIG. 2.
Figure 4:
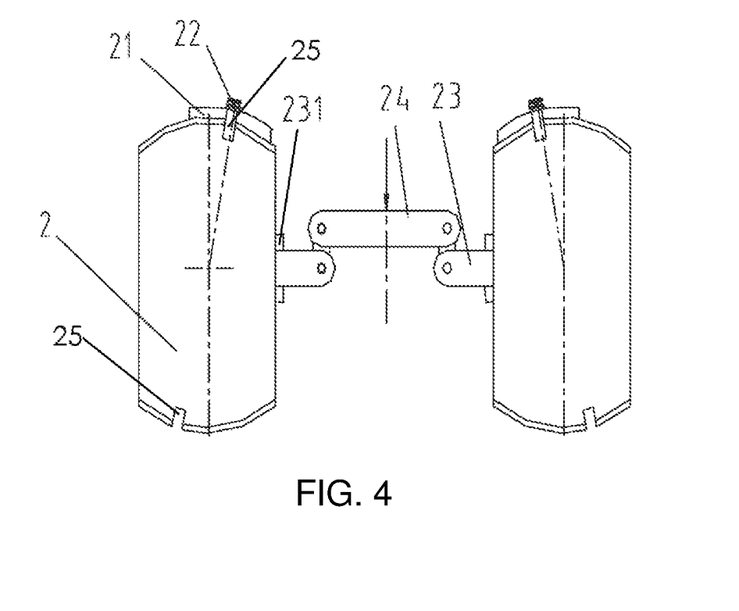
FIG. 4 is a schematic view of tangential load distribution.

As shown in FIG. 3 and FIG. 4, in the present application, a tangential load distribution beam 24 capable of receiving a tangential load is provided on each bottom of the first tangential load actuator 3 and the second tangential load actuator 4, and each of the tangential load distribution beam 24 is horizontally arranged in front and rear direction and is vertical to the upright columns; two ends of the tangential load distribution beam 24 are respectively connected to the simulated wheels 2 which are arranged on the front side and the rear side of the upright columns, so as to distribute a tangential load to the simulated wheels 2 arranged on the two sides of the tangential load actuator. As one embodiment, the simulated wheels 2 are symmetrically arranged, so that the tangential load distribution beam 24 can, after receiving the tangential load, evenly distribute the tangential load to the two ends.

As shown in FIG. 4, the tangential load is applied to the tangential directions of the tread radius circumferences of the simulated wheels 2, round pins are provided at the horizontal radius of the simulated wheels 2 to be respectively connected to the two ends of the tangential load distribution beam 24.

In addition, in the present application, in order to be adapted to simulated wheels of various types and to reduce the number of times for replacing simulated wheels, the simulated wheels 2 in the present application are preferably drum-shaped, i.e., one simulated wheel 2 includes two opposite end surfaces vertically arranged, and two arc surfaces connecting the two end surfaces together. When the simulated wheel 2 is mounted, the arc surfaces of the simulated wheels 2 are placed as one is at top, and the other is at bottom. The arc surfaces of the drum-shaped simulated wheel are arc treads with different diameters. In this way, when wheels of different diameters are to be simulated, wheels of two different diameters can be simulated on a same simulated wheel just by rotating by a certain angle. In order to further illustrate the advantages of the drum-shaped simulated wheels in the present application, a specific embodiment is described as an example. In order to perform a fatigue test on L-B brake beams (a wheel diameter of 840 mm, and a deflection angle of the centerline of the brake shoe holder of 12°) and L-B1 brake beams (a wheel diameter of 915 mm, and a deflection angle of the brake shoe holder of 14°), two arc treads with a diameter of 840 mm and of 915 mm are respectively designed on the simulated wheel. The switching between two wheel diameters can be realized just by rotating the simulated wheel by 180°.

Further referring to FIG. 4, baffles (located inside the simulated wheels, not shown) are provided in a front wheel and a rear wheel of the simulated wheels 2; and connection beams 23 mountable with the tangential load distribution beam 24 are mounted in the baffles and fixed by wedges 231.

A simulated brake shoe 21 matched with the radian of the tread is provided on the tread of the simulated wheel 2, a brake shoe holder 10 of a brake beam is provided on the simulated brake shoe 21, and a trapezoidal gap elimination device 22 is provided between the simulated wheel 2 and the brake shoe holder 10 so as to eliminate the gap between the brake shoe holder 10 and the simulated wheel 2. As another embodiment, a U-shaped groove 25 is formed on the simulated wheel 2 and configured to receive a lower portion of the gap elimination device 22. Here, for the convenience of placing the gap elimination device 22, a brake shoe back 211 of the simulated brake shoe 21 is removed. That is, the simulated brake shoe 21 is a brake shoe divided into segments, and an upper portion of the gap elimination device 22 is located in the trapezoidal groove of the brake shoe holder 10, and the lower portion thereof is located in the U-shaped groove 25.

The simulated wheel 2 in the present application may be made of steel plates by welding, a center hole is formed of round steel by a turn-milling process, and a web is simulated by two steel plates of 16 mm Since only the contact area of the tread with the simulated brake shoe 21 is used, the simulated wheel 2 is drum-shaped and part of the circumference is removed to provide for points on which the tangential load acts, and a U-shaped groove 25 is formed, so as to connect the simulated wheel with the brake shoe holder of the brake beam by the gap elimination device. To coordinate with the simulated wheel tread, the cross rod 61 of the brake beam 6 is not linear, but with a slope of 1:20. In this way, a slope of 1:20 is thus caused on a brake shoe mounting surface. The tread portion of the simulated wheel in the present application has a conical degree of 1:20 so that, after the simulated brake shoe 21 is mounted on the brake shoe holder 10, gap-free coordination is formed between the simulated brake shoe 21 and the simulated wheel 2. In addition, in order to achieve the gap-free coordination, in the embodiments of the present application, an upper surface and a lower surface of the simulated brake shoe 21 are a cylindrical surface and a conical surface capable of coordinating with the brake shoe holder and the simulated wheel 2, respectively.

Figure 5:
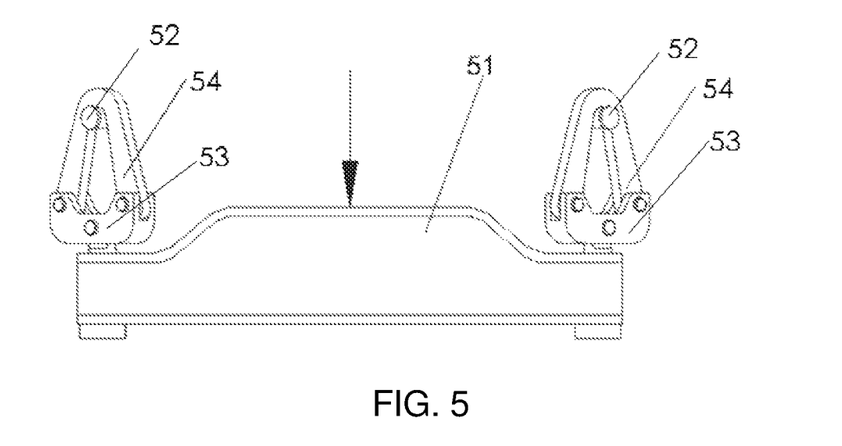
FIG. 5 is a schematic view of pressure load distribution.

FIG. 5 is a schematic view of pressure load distribution in the present application. A pressure load distribution beam 51 capable of distributing a pressure load is provided on the bottom of the pressure load actuator 5, with the pressure load distribution beam 51 being horizontally arranged in front and rear direction and being vertical to the upright columns, wherein round strut pins 52 capable of having brake beam struts 63 mounted thereon are mounted at two ends of the pressure load distribution beam 51; and the brake beam struts 63 are mounted on the round strut pins 52 to receive the pressure load distributed by the pressure load actuator 5.

As another embodiment, as shown in FIG. 5, a pressure load distribution beam 51 capable of distributing a pressure load is provided on the bottom of the pressure load actuator 5, with the pressure load distribution beam 51 being horizontally arranged in front and rear direction and being vertical to the upright columns; U-shaped connection blocks 53 are symmetrically provided at both ends of the pressure load distribution beam 5, and an inverted V-shaped strut connection block 54 is provided above each U-shaped connection block 53; two ends of one U-shaped connection block 53 are connected to the two ends of one strut connection block 54; a round strut pin 52 is provided on the strut connection block 54; the beam strut 63 of a brake beam is arranged on the round strut pin 52 and maintained vertical.

In the above description, the pressure load actuator 5 evenly applies a load to the two beam struts 63 of two brake beams by the pressure load distribution beam 51, and two ends of the pressure load distribution beam 51 are respectively connected to the round strut pins 52. This makes the maximum load of the pressure load actuator 5 twice of the stipulated pressure load. When a pressure load is transferred, the places where the beam struts 63 and the pressure load actuator 5 are connected are connected by pins (round strut pins 52). This has the following advantages that welding members are reduced, processing members are increased, and the assembly precision is improved. Meanwhile, the structure can be slightly rotated around the round strut pins 53 and the acting distance of the force can remain unchanged. Incoordination for mounting pieces to be tested, which is caused by the manufacturing tolerance and assembly tolerance of the brake beams, can be effectively solved, and meanwhile, the loading precision can be guaranteed.

As shown in FIG. 2, as another embodiment, a feedback device 7 capable of performing feedback tests on the tangential load is provided on the bottom of the first tangential load actuator 3, and the feedback device 7 includes a sensor capable of sensing the intensity of a tangential load feedback force.

In order to make the structure of the present application more firm, diagonal braces 11 can also be provided in an inclined manner on a front side and a rear side of the upright columns For the convenience of maintenance, stepladders for users to walk thereon can be provided on the left side of the first upright column 81 and the right side of the fourth upright column 84, and a platform is horizontally provided on the top of the upright columns for the maintenance and mounting of the structure in the present application.

Figure 6:
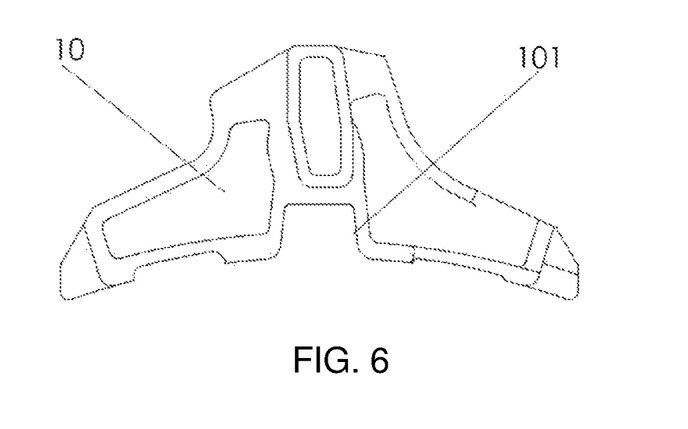
FIG. 6 is a schematic structure diagram of a brake shoe holder.
Figure 7:
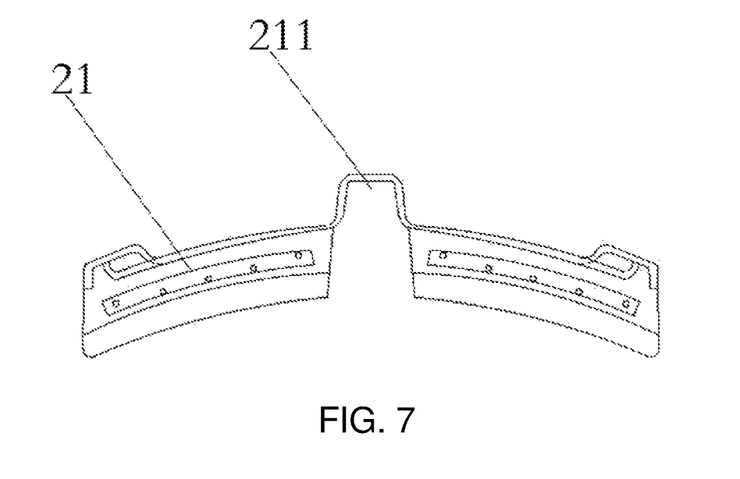
FIG. 7 is a schematic structure diagram of a brake shoe.

In the prior art, a brake shoe for vehicles is mounted on a brake shoe holder 10, the brake shoe and the brake shoe holder 10 are connected by a brake shoe pin, and the brake shoe is located on the inner side of the brake shoe holder 10. As shown in FIG. 7, there is a trapezoidal brake shoe back 211 protruding outward on the brake shoe. As shown in FIG. 6, an inward concave trapezoidal groove 101 capable of matching with the brake shoe back 211 on the brake shoe 21 is provided on the bottom of the brake shoe holder 10. That is, the connection portion between the brake shoe back 211 and the trapezoidal groove 101 is trapezoidal. As a preferred embodiment, when a fatigue test is performed on the brake beam, in order to ensure the arrangement of the gap elimination device, the brake shoe back 211 of the simulated brake shoe 21 is removed in this embodiment. That is, the simulated brake shoe 21 is a brake shoe divided into two separated segments. The simulated brake shoe 21 is located at the inner side of the brake shoe holder 10 and between the brake shoe holder 10 and the simulated wheel 2, and a gap elimination device 22 is provided between the brake shoe holder 10 and the simulated wheel 2, so as to guarantee the test loading frequency and avoid the additional impact in the test.

Figure 8:
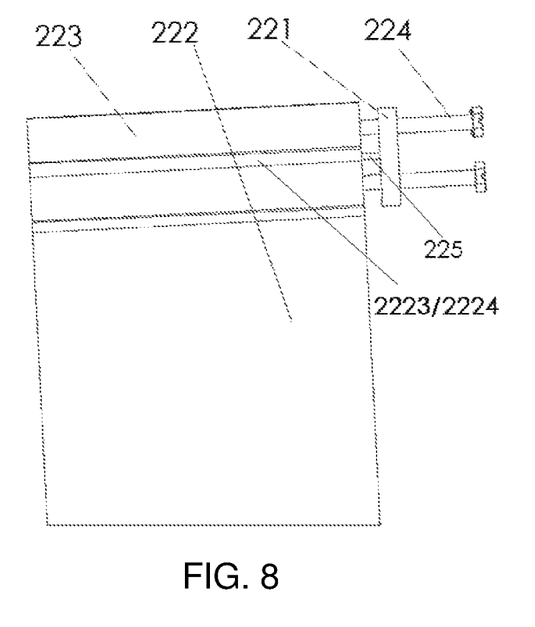
FIG. 8 is a front view of a gap elimination device.
Figure 9:
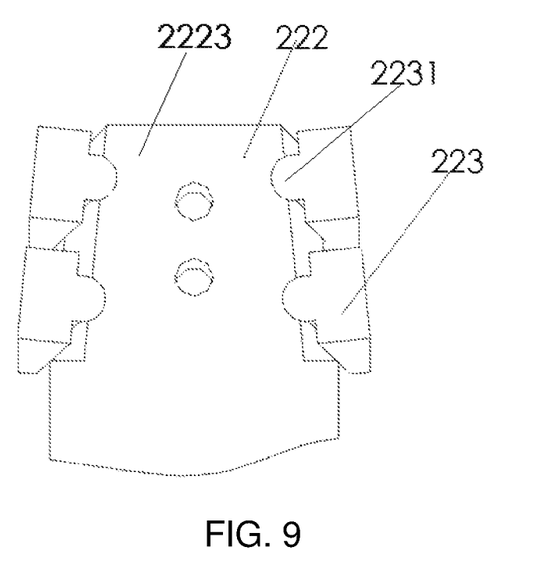
FIG. 9 is a side view of partial structure of the gap elimination device.
Figure 10:
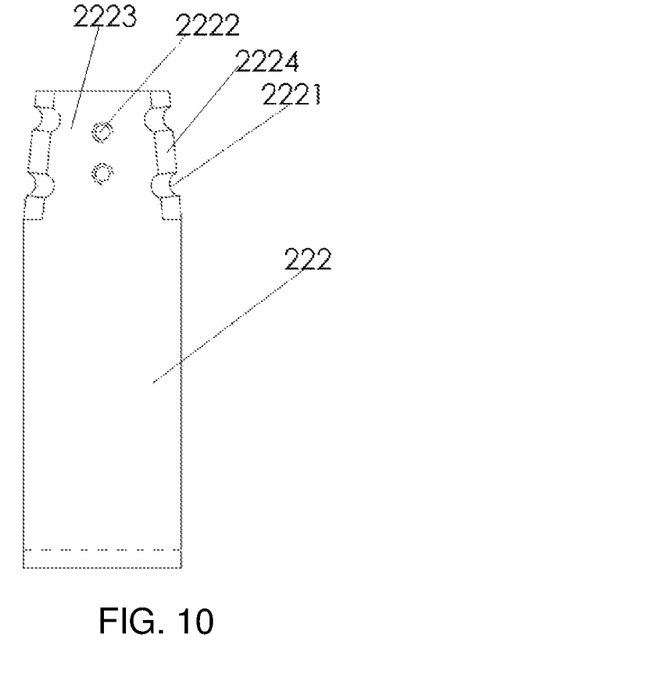
FIG. 10 is a side view of a connection block.

FIG. 8 and FIG. 9 are respectively a front view and a side view of the gap elimination device in the present application (based on FIG. 2). The gap elimination device 22 in the drawing, which can be used to eliminate a gap between the simulated wheel 2 and the brake shoe holder 10 during a brake beam fatigue stand test, comprises a connection block 222 capable of connecting the simulated wheel 2 and the brake shoe holder 10. A top part of the connection block 222 is a trapezoidal end 2223 matched with the trapezoidal groove 101 of the brake shoe holder 10, and two sides of the trapezoidal end 2223 are slope surfaces 2224 (as shown in FIG. 10). An open groove 2221 is formed on the slope surface 2224. An adjustment block 223 which is movable in the open groove 2221 is matched in the open groove 2221, and a gap between the side of the top of the connection block and the brake shoe holder 10, i.e., a gap between the slope surface 2224 and the trapezoidal groove 101 of the brake shoe holder, is eliminated by moving the position of the adjustment block 223 inside the open groove 2221. Exactly, an upper part of the connection blocks 222 is the trapezoidal end 2223 matching with the trapezoidal groove 101 of the brake shoe holder 10, as shown in FIG. 9 and FIG. 10.

Figure 11:
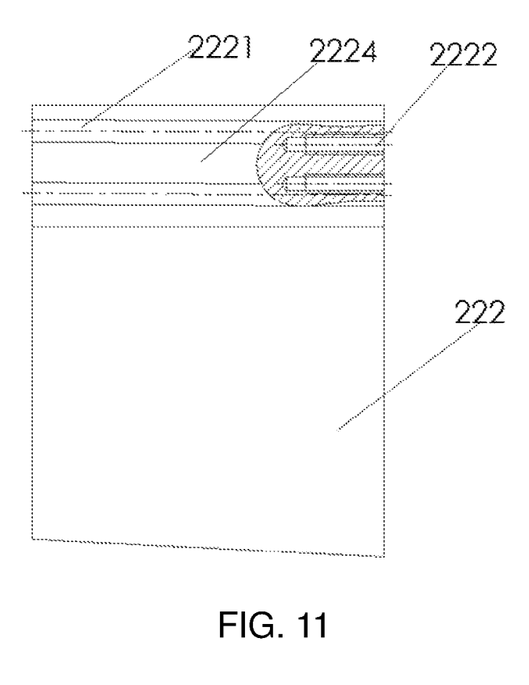

FIG. 10 and FIG. 11 are respectively the side view and the front view of the connection block. As one embodiment, the open groove 2221 is arranged along a slope direction of the slope surface 2224 of the trapezoidal end, preferably passing through a front end surface and a rear end surface of the connection block 222. The open groove 2221 is a semi-arc groove. A semi-cylindrical protrusion 2231 matched with the open groove 2221 is provided on the adjustment block 223.

As one embodiment, the thickness of the adjustment block 223 decreases inward from the surface of the trapezoidal end 2223, and the variation slope thereof is opposite to the slope surface 2224. FIG. 9 shows a state in which the thickness of the adjustment block 223 becomes thinner from the front to the back. In this way, when a gap is to be eliminated, the position of the adjustment block 223 is adjusted, so that the protrusion 2231 moves inward along the open groove 2221. There is always a position where an outer side of the adjustment block 223 and a side of the trapezoidal groove 101 of the brake shoe holder are parallel to and contact with each other. The operating principle is similar to that of a wedge.

In addition, the open groove 2221 and the protrusion 2231 are preferably semi-arc, with the following advantages: due to the contact of arc surfaces, when the position is to be adjusted, there is a certain rotational degree of freedom and the rotation thus becomes easier. This is suitable for contact surfaces having slopes caused by different tolerances.

Meanwhile, for the convenience of adjusting the movement of the adjustment block 223 and fixing the adjustment block 223, an adjustment plate 221 is mounted on one side of the trapezoidal end 2223 so as to prevent the adjustment block 223 from loosening (as shown in FIG. 8).The connection block 222 and the adjustment block 221 are fixedly connected, preferably fixed by a bolt 225. An adjustment bolt 224 is provided on the adjustment plate 221 and located on one side of the adjustment block 223. As shown in FIG. 8, the adjustment bolt 224 is configured to adjust the adjustment block 223 to move along the open groove 2221, and the adjusted adjustment block 223 is compacted tightly by the adjustment bolt 224, so as to prevent the adjustment block 223 from shifting due to the vibration during the test. Of course, it is easy for a person skilled in the art to come up with an idea of forming a mounting hole 2222 on the end surface of the connection block 222 in order to mount the bolt 225 of the adjustment plate 223, which will not be repeated here.

As a preferred embodiment, there are two open grooves 2221 formed on each side of the connection block 222, i.e., on the slope surface 2224. Correspondingly, the number of the adjustment blocks 223 increases. The advantage lies in that the contact area between the adjustment block 223 and the trapezoidal groove 101 of the brake shoe holder can be increased, and the brake shoe holder 10 and the simulated wheel 2 can be better restricted and force can be better transferred.

In addition, the brake shoe holder 10 has a certain slope itself. In the prior art, the slope of the mounting surface of the brake shoe holder 10 is generally 1:20. In order to match this slope, the top surface of the connection clock 222 is arranged as an inclined surface consistent with the mounting surface of the brake shoe holder 10. When the slope is 1:20, adjusting a gap of 1 mm requires an inward movement of the adjustment block 223 by 20 mm The mounting space of the device can completely meet the requirement on the movement of the cylindrical adjustment block 223.

In order to further illustrate the role of the gap elimination device in eliminating a gap during a brake beam fatigue test, the specific mounting process of the gap elimination device is incorporated for further description below.

During a brake beam fatigue test, a groove is formed on the tread of the simulated wheel 2, and the connection block 222 is embedded thereto; the simulated brake shoe 21 (with the brake shoe back 211 removed) is mounted on the simulated wheel tread by welding or compacting by bolts; the brake shoe holder 10 of the brake beam is mounted on an upper side of the simulated brake shoe 21; the upper portion of the connection block 222 is mounted inside the trapezoidal groove 101 of the brake shoe holder, and the lower portion of the connection block 222 is mounted in the U-shaped groove 25; adjustment blocks 223 are mounted at two ends of the connection block 222, the position of the adjustment block 223 in the connection block 222 is adjusted until the adjustment block 223 is initially fitted with the trapezoidal groove 101 of the brake shoe holder, and the adjustment plate 221 is then fixedly mounted; the fitting between the adjustment block 223 and the trapezoidal groove 101 of the brake shoe holder is further facilitated by adjusting the adjustment bolts 224, or the adjustment bolt 224 can be used for fixing the two after they are fit with each other.

Meanwhile, in order to show the mounting convenience of the present application, description will be given with reference to the specific mounting processes of the brake beam fatigue test stand.

First, the pressure load actuator 5 is retracted, and two jacks can be used to slightly jack-up the pressure load loading beam to mount the brake beams 6 conveniently.

After the brake beams 6 are placed at an approximate position by a crane or manually, an inner side of the cross rod 62 thereof is slightly adjusted to contact a positioning rod. The beam struts 63 are maintained in the upright direction and located above the pressure load distribution beam 51 (a plumb can be used, if necessary), the brake shoe holders on two sides can be fitted with the simulated brake shoes 21 by curved surfaces. Now, the brake beams 6 have been positioned, but not yet been fixed.

By adjusting the adjustment bolts 224, the gap is eliminated by the gap elimination device 22. A gap elimination block between a guide bushing and a simulated chute is adjusted to eliminate the gap at a position restricted by the guide bushing.

A strut connection block 54 is passed through the beam strut 63 and through the round strut pin 52 and the U-shaped connection block 53, and meanwhile, the beam strut 63 is fixed on the round strut pin 52.

After the mounting operations above are all performed on the brake beams 6 on the two sides, the jacks can be lowered and removed. If slight adjustment is required during the mounting process, the adjustment should be performed after the gap elimination device 22 is loosened.

The tangential load distribution beam 24 is examined and adjusted to be horizontal, and the load of the tangential load actuator is zero.

Finally, a comprehensive examination is performed to ensure that all the connections are properly mounted. So far, the mounting has been completed.

To simulate brake beams of other types, the simulation can be achieved by repeating the above mounting steps after rotating the simulated wheels by 180°.

After the brake beams 6 are properly mounted on the test stand, the beam struts 63 thereof are in the vertical state; and during the test, the loads applied to the brake beams 6 as the driving power are a pressure load and tangential loads. After the pressure load is applied to the beam struts 63, the load is finally transferred onto the simulated wheels 2, so that the simulated wheel 2 bear a load and torque which are vertical downward. The loads are balanced by counter force of a support of the simulated wheel 2 and the simulated chute; and the torque caused by the tangential load is also balanced by the counter-force provided by the simulated chute.

During the test, there are total three positions with load acting, respectively: the actuator provides a counter-force onto the upper side of the test stand; lower ends of the tangential load actuators act on the tangential load distribution beams 24 and finally on the base 1 on which the simulated wheels are mounted; and the load of the pressure load actuator 5 in the vertical direction acts on the pressure load distribution beam 51 and finally on the simulated wheels 2 via the brake beams 6.

What is claimed is:

1. A brake beam fatigue test stand, for simultaneously testing a fatigue strength of two brake beams, comprising: a base, and four upright columns vertical to the base and arranged on the base at intervals; wherein, from a left side to a right side of the base successively, there are a first upright column, a second upright column, a third upright column and a fourth upright column, wherein,
   a first tangential load actuator capable of applying a tangential load is mounted vertically between the first upright column and the second upright column, with simulated wheels being mounted on a front side and a rear side of a bottom of the first tangential load actuator;
   a pressure load actuator capable of applying a pressure load is mounted vertically between the second upright column and the third upright column;
   a second tangential load actuator capable of applying a tangential load is mounted vertically between the third upright column and the fourth upright column, with simulated wheels being mounted on a front side and a rear side of a bottom of the second tangential load actuator; the second tangential load actuator and the first tangential load actuator are symmetrically arranged by taking the pressure load actuator as a center; and,
   the two brake beams are uprightly mounted on a front side and a rear side of the upright columns, with two ends of the brake beam being supported on treads of the simulated wheels.

2. The brake beam fatigue test stand according to claim 1, wherein a tangential load distribution beam capable of receiving the tangential load is provided on each bottom of the first tangential load actuator and the second tangential load actuator, and each of the tangential load distribution beams is horizontally arranged and is vertical to the upright columns; two ends of the tangential load distribution beam are respectively connected to the simulated wheels arranged on the front side and the rear side of the upright columns, to distribute the tangential load to the simulated wheels arranged on the two sides of the tangential load actuators.

3. The brake beam fatigue test stand according to claim 2, wherein baffles are provided in a front wheel and a rear wheel of the simulated wheels; and connection beams mountable with the tangential load distribution beam are mounted in the baffles and fixed by wedges.

4. The brake beam fatigue test stand according to claim 2, wherein each of the simulated wheels is drum-shaped, and an upper arc surface and a lower arc surface of each drum-shaped simulated wheel are arc treads with different diameters, to simulate wheels of two different diameters on a same simulated wheel.

5. The brake beam fatigue test stand according to claim 2, wherein a simulated brake shoe matched with a radian of the tread is provided on the tread of each simulated wheel; a brake shoe holder is provided on each simulated brake shoe, and a gap elimination device is provided between simulated wheel and the brake shoe holder to eliminate a gap between the brake shoe holder and the each simulated wheel.

6. The brake beam fatigue test stand according to claim 5, wherein the gap elimination device comprises a connection block capable of connecting a corresponding simulated wheel and the brake shoe holder; a top part of the connection block is a trapezoidal end matched with a trapezoidal groove on the brake shoe holder, and two sides of the trapezoidal end are slope surfaces; an open groove is formed on the slope surface; and an adjustment block which is movable in the open groove is provided in the open groove, and a gap between a side of the top part of the connection block and the brake shoe holder is eliminated by moving the position of the adjustment block inside the open groove.

7. The brake beam fatigue test stand according to claim 6, wherein a protrusion is provided on an inner surface of the adjustment block, and the slope surface has a slope direction opposite to a slope direction of the inner surface of the adjustment block.

8. The brake beam fatigue test stand according to claim 6, wherein the open groove is arranged along the slope direction of the slope surface, the open groove is a semi-arc groove, and a semi-cylindrical protrusion matched with the open groove is provided on the adjustment block.

9. The brake beam fatigue test stand according to claim 2, wherein a pressure load distribution beam capable of distributing the pressure load is provided on a bottom of the pressure load actuator; the pressure load distribution beam is horizontally arranged and is vertical to the upright columns, wherein round strut pins capable of having brake beam struts mounted thereon are mounted at two ends of the pressure load distribution beam; and the beam struts of the brake beam are mounted on the round strut pins to receive the pressure load distributed by the pressure load actuator.

10. The brake beam fatigue test stand according to claim 9, wherein U-shaped connection blocks are provided at both ends of the pressure load distribution beam, and an inverted V-shaped strut connection block is provided above each U-shaped connection block; two ends of one U-shaped connection block are connected to two ends of one strut connection block; a round strut pin is provided on the strut connection block; the round strut pin is configured to maintain the beam strut of the brake beam vertical and transfers the pressure load to the brake beam.

11. The brake beam fatigue test stand according to claim 1, wherein each of the simulated wheels is drum-shaped, and an upper arc surface and a lower arc surface of each drum-shaped simulated wheel are arc treads with different diameters, to simulate wheels of two different diameters on a same simulated wheel.

12. The brake beam fatigue test stand according to claim 11, wherein a simulated brake shoe matched with a radian of the tread is provided on the tread of each simulated wheel; a brake shoe holder is provided on the simulated brake shoe, and a gap elimination device is provided between each simulated wheel and the brake shoe holder to eliminate a gap between the brake shoe holder and each simulated wheel.

13. The brake beam fatigue test stand according to claim 1, wherein a simulated brake shoe matched with a radian of the tread is provided on the tread of each simulated wheel; a brake shoe holder is provided on the simulated brake shoe, and a gap elimination device is provided between each simulated wheel and the brake shoe holder to eliminate a gap between the brake shoe holder and each simulated wheel.

14. The brake beam fatigue test stand according to claim 13, wherein the gap elimination device comprises a connection block capable of connecting a corresponding simulated wheel and the brake shoe holder; a top part of the connection block is a trapezoidal end matched with a trapezoidal groove on the brake shoe holder, and two sides of the trapezoidal end are slope surfaces; an open groove is formed on the slope surface; and an adjustment block which is movable in the open groove is provided in the open groove, and a gap between a side of the top part of the connection block and the brake shoe holder is eliminated by moving the position of the adjustment block inside the open groove.

15. The brake beam fatigue test stand according to claim 14, wherein a protrusion is provided on an inner surface of the adjustment block, and the slope surface has a slope direction opposite to a slope direction of the inner surface of the adjustment block.

16. The brake beam fatigue test stand according to claim 14, wherein the open groove is arranged along the slope direction of the slope surface, the open groove is a semi-arc groove, and a semi-cylindrical protrusion matched with the open groove is provided on the adjustment block.

17. The brake beam fatigue test stand according to claim 14, wherein an adjustment plate capable of preventing the adjustment block from loosening is mounted on a side of the trapezoidal end of the connection block, and the connection block and the adjustment plate are connected by bolts.

18. The brake beam fatigue test stand according to claim 1, wherein a pressure load distribution beam capable of distributing the pressure load is provided on a bottom of the pressure load actuator; the pressure load distribution beam is horizontally arranged and is vertical to the upright columns, wherein round strut pins capable of having brake beam struts mounted thereon are mounted at two ends of the pressure load distribution beam; and the beam struts of the brake beam are mounted on the round strut pins to receive the pressure load distributed by the pressure load actuator.

19. The brake beam fatigue test stand according to claim 18, wherein U-shaped connection blocks are provided at both ends of the pressure load distribution beam, and an inverted V-shaped strut connection block is provided above each U-shaped connection block; two ends of one U-shaped connection block are connected to two ends of one strut connection block; a round strut pin is provided on the strut connection block; the round strut pin is configured to maintain the beam strut of the brake beam vertical and transfers the pressure load to the brake beam.

20. The brake beam fatigue test stand according to claim 1, wherein a feedback device capable of performing feedback tests on the tangential load is provided on the bottom of the first tangential load actuator, and the feedback device comprises a sensor capable of sensing the intensity of a tangential load feedback force.

* * * * *